United States Patent
Madabhushi et al.

(10) Patent No.: US 6,646,084 B2
(45) Date of Patent: Nov. 11, 2003

(54) POLYACRYLAMIDE MEDIUM FOR THE ELECTROPHORETIC SEPARATION OF BIOMOLECULES

(75) Inventors: Ramakrishna S. Madabhushi, Fremont, CA (US); Stuart A. Gammon, Tracy, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/094,397

(22) Filed: Mar. 7, 2002

(65) Prior Publication Data

US 2002/0128415 A1 Sep. 12, 2002

Related U.S. Application Data

(60) Provisional application No. 60/274,360, filed on Mar. 8, 2001.

(51) Int. Cl.$^7$ .............................................. C08F 120/54
(52) U.S. Cl. .................... 526/303.1; 526/217; 526/225
(58) Field of Search ................................ 526/217, 225, 526/303.1

(56) References Cited

U.S. PATENT DOCUMENTS

| | | | |
|---|---|---|---|
| 3,332,922 A | 7/1967 | Hoover | |
| 4,282,340 A | 8/1981 | Anchor et al. | |
| 4,473,689 A | 9/1984 | Login et al. | |
| 4,617,359 A | 10/1986 | Smith | |
| 5,306,404 A | 4/1994 | Notsu et al. | |
| 5,464,516 A * | 11/1995 | Takeda et al. | 204/182.9 |
| 6,228,988 B1 * | 5/2001 | Floyd et al. | 536/22.1 |
| 2001/0027921 A1 * | 10/2001 | Chan et al. | 204/469 |

FOREIGN PATENT DOCUMENTS

EP 0677537 B1 7/1999

OTHER PUBLICATIONS

Carrilho et al Analytical Chemistry 1996, 68, 3305–3313.
Salano et al Analytical Chemistry 1998, 70, 3996–4003.
Goetzinger et al Electrophoresis 1998, 19, 242–248.
Yu Fang et al Electrophoresis 1996, 17, 1436–1442.
Grossman, P.D. J. Chromotography A, 1994, 663, 219–227.
Ruiz–Martinez et al Analytical Chemistry 1993, 65, 2851–2858.
A. Moulik Chemical Abstracts Search Results Nov. 30, 2000.
A. Moulik Further Search Results Dec. 14, 2000.
R. Madabhushi Separation of 4–color DNA sequencing extension products in noncovalently coated capillaries using low viscosity polymer solutions 1998, 19, 224–230.

* cited by examiner

Primary Examiner—Helen L. Pezzuto
(74) Attorney, Agent, or Firm—Michael C. Staggs; Alan H. Thompson

(57) ABSTRACT

A polyacrylamide medium for the electrophoretic separation of biomolecules. The polyacrylamide medium comprises high molecular weight polyacrylamides (PAAm) having a viscosity average molecular weight ($M_v$) of about 675–725 kDa were synthesized by conventional red-ox polymerization technique. Using this separation medium, capillary electrophoresis of BigDye DNA sequencing standard was performed. A single base resolution of ~725 bases was achieved in ~60 minute in a non-covalently coated capillary of 50 μm i.d., 40 cm effective length, and a filed of 160 V/cm at 40° C. The resolution achieved with this formulation to separate DNA under identical conditions is much superior (725 bases vs. 625 bases) and faster (60 min. vs. 75 min.) to the commercially available PAAm, such as supplied by Amersham. The formulation method employed here to synthesize PAAm is straight-forward, simple and does not require cumbersome methods such as emulsion polymerizaiton in order to achieve very high molecular weights. Also, the formulation here does not require separation of PAAm from the reaction mixture prior to reconstituting the polymer to a final concentration. Furthermore, the formulation here is prepared from a single average mol. wt. PAAm as opposed to the mixture of two different average mo. wt. PAAm previously required to achieve high resolution.

25 Claims, No Drawings

POLYACRYLAMIDE MEDIUM FOR THE ELECTROPHORETIC SEPARATION OF BIOMOLECULES

RELATED APPLICATION

This application relates to U.S. Provisional Application No. 60/274,360 filed Mar. 8, 2001, and claims priority thereof.

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to electrophoretic separation of biomolecules, particularly to polyacrylamide medium to electrophoretically separate DNA sequencing extension products by capillary electrophoresis, and more particularly to high molecular weight polyacrylamides having a viscosity average molecular weight of around 675–725 kDa synthesized by conventional red-ox polymerization technique for electrophoretic separation of DNA or other biomolecules.

Capillary electrophoresis (CE) of DNA requires some type of non-charged polymer solution due to free-draining coil behavior of DNA. Addition of polymer to the separation medium changes, the frictional drag of DNA thereby making mobility of DNA a function of its size.

Polyacrylamide (PAAm) is one of the popular polymer in preparing separation medium for DNA sequencing by CE. The objective was to achieve high-resolution and long read-lengths in short run-times while keeping the solution viscosity to moderate levels. However, so far the objective is met with partial degree of success only. Furthermore, routine synthesis and uniform dilution of PAAm to a given final concentration is problematic and takes a long time. Grossman, J. Chromatograph A, 1994, 663, 219–227, reported the use of low molecular weight PAAm solution, but the PAAm needed to be isolated from the polymerization mixture before it was reconstituted to the final concentration.

Low concentrations of high molecular weight PAAm were used by Carrilho, E. et al., Anal. Chem., 1996, 68,3305–3313, and reported a read-length of ~1000 bases at a resolution value of 0.1. However, the PAAm stock solution takes 2–3 days for uniform dilution to a final concentration, which therefore is inconvenient and time-consuming. Goetzinger, W., et al., Electrophoresis, 1998, 19, 242–248, reported the advantages of high molecular weight PAAm made by well known emulsion polymerization technique to make uniform dilution of PAAm more convenient. Further optimization of the separation media to increase the performance was attempted by Salas-Solano, O. et al., Anal. Chem., 1998, 70,4003,3996–4003, using a mixture of two different average molecular weights of PAAm and reported a read-length of ~1000 bases (resolution value not reported). In both latter cases, PAAm needed to be separated and purified before reconstituting to a final concentration which makes the process less than ideal for production environment.

However, consistency in synthesizing high molecular weight PAAm is still a challenge. This problem compromises high-resolution and long read-lengths. To circumvent this problem, Solano et al referenced above, used PAAm synthesized from well known emulsion polymerization methods. However, this method is cumbersome and requires the separation and purification of PAAm from the polymerization mixture before it can be reconstituted. Furthermore, these prior methods also needed two different average molecular weight PAAm(s) to achieve the desired high-resolution.

The present invention provides a solution to the above referenced problems, and comprises a simple and consistent formulation or method of making very high molecular weight PAAm. Separation medium formulated from the polymer of this invention has yielded better resolution than the commercially supplied medium, such as that commercialized by Amersham Pharmacia (Molecular Dynamics, Sunnyvale, Calif.) under identical separation conditions. Here, we report a simple formulation of PAAm separation medium, based on a single average molecular weight PAAm synthesized from conventional red-ox polymerization method. The PAAm stock solution was made to uniform dilution in ~24 hours to the final concentration. Additionally, this formulation has better performance than the commercially supplied PAAm medium from Amersham Pharmacia making it convenient and potentially cost-effective in a production sequencing environment. For example, the resolution achieved with the formulation of the present invention to separate DNA under identical conditions is much superior (725 bases vs. 625 bases) and faster (60 min. vs. 75 min.) to the commercially supplied product from Amersham Pharmacia. Using the present invention, high molecular weight PAAm having a viscosity average molecular weight ($M_v$) of 674 kDa were synthesized by conventional red-ox polymerization technique.

SUMMARY OF THE INVENTION

It is an object of the present invention to provide polyacrylamide medium for electrophoretic separation of biomolecules.

A further object of the invention is to enable synthesizing high molecular weight polyacrylamide for capillary electrophoresis.

A further object of the invention is to provide a simple and consistent method of making very high molecular weight polyacrylamide.

Another object of the invention is to provide high molecular weight polyacrylamides having a viscosity average molecular weight of around 675–725 kDa which are synthesized by conventional red-ox polymerization techniques.

Another object of the invention is to provide a high molecular weight polyacrylamide that provides a resolution for separate DNA that is superior (725 bases) and faster (60 min.) to the commercially available polyacrylamides.

Another object of the invention is to provide a method for producing high molecular weight polyacrylamides which is straight-forward, simple, and does not require cumbersome processing such as emulsion polymerization.

Another object of the invention is to provide a method for producing a polyacrylamide medium which does not require separation of the polyacrylamide from the reaction mixture prior to reconstituting the polymer to a final concentration.

Another object of the invention is to provide a polyacrylamide formulation which is prepared from a single average molecular weight polyacrylamide as opposed to the mixture of two different average molecular weight polyacrylamides required to achieve high resolution by prior known approaches.

Other objects and advantages of the present invention will become apparent from the following description. The present invention involves a high molecular weight polyacrylamide medium for the electrophoretic separation of biomolecules, such as DNA. In accordance with the present invention, high molecular weight polyacrylamides (PAAM) having a viscosity average molecular weight ($M_v$) of around 675–725 kDa were synthesized by a conventional red-ox polymerization technique. This is achieved by optimizing the concentrations of acrylamide monomer, ammonium persulfate (APS), and tetramethylithylenediamine (TEMED) and polymerizing in aqueous medium in presence of urea at sub-ambient temperatures after efficiently removing oxygen from the reaction mixture by bubbling ultra-pure argon. The resultant polymer solution is further diluted to a suitable final concentration with an electrophoretic buffer, such as TRIS-TAPS-EDTA (TTE). The methods employed here to synthesize PAAm is straight-forward, simple and does not require cumbersome methods such as emulsion polymerization in order to achieve very high molecular weights. The method here also does not require separation of PAAm from the reaction mixture prior to reconstituting the polymer to a final concentration.

Furthermore, the formulation is prepared from a single average mol. wt. PAAm as opposed to the mixture of two different average mol. wt. PAAm required to achieve high resolution, as reported in the above-referenced article by Solano et al. Thus, the present invention provides consistency in synthesizing high molecular weight PAAm, thereby providing a solution to the above-discussed problems of the prior known synthesizing approaches.

DETAILED DESCRIPTION OF THE INVENTION

The present invention is directed to polyacrylamide (PAAm) medium for the electrophoretic separation of biomolecules, such as DNA, and involves the use of and method for the formation of high molecular weight PAAm. While PAAm has been widely used in electrophoretic separation of biomolecules, and its copolymers have been used in viscosity index improves for enhanced oil recovery, the invention provides high molecular weight PAAm which are synthesized in a straight-forward, simple formulation approach and does not require cumbersome methods such as emulsion polymerization. Also, the formulation approach of this invention does not require separation of PAAm from the reaction mixture prior to reconstituting the polymer to a final concentration which is exemplified as 2% to 4%. Furthermore, the formulation of this invention is prepared from a single viscosity average mol. wt. PAAm (500 kDa to 1000 kDa) as opposed to the mixture of two different average mol. Wt. PAAm (e.g. 50 kDa and 9 MDa) required to achieve high resolution as in the previously known formulation approaches.

By this invention, high molecular weight PAAm having a viscosity average molecular weight ($M_v$) of 674 kDa (about 675 kDa to about 725 kDa) was synthesized by conventional red-ox polymerization technique. The red-ox polymerization technique basically involves polymerizing acrylamide with ammonium persulfate-TEMED system. This was achieved by optimizing the concentration of acrylamide monomer, ammonium persulfate (APS), and tetramethylethylenediamine (TEMED) and polymerizing in aqueous medium, in presence of 7 M urea at 7° C. or at sub-ambient temperatures (0 to 7° C.) after efficiently removing oxygen from the reaction mixture by bubbling ultra-pure argon or helium. The resultant PAAm stock solution was further diluted to a suitable final concentration of 3% (w/v), PAAm having 7M urea with an electrophoretic buffer, such as TRIS-TAPS-EDTA (TTE) or Trisborate (TBE). Using this separation medium capillary electrophoresis (CE) of Big Dye DNA sequencing standard was performed with an ABI 310 Genetic Analyzer, manufactured by Applied Biosystems (Foster City, Calif.). The Big Dye DNA sequencing standard is defined as DNA sequencing standard. A single base resolution of ~725 bases was achieved with a resolution value of 0.59 in ~60 minutes at 40° C. in a non-covalently coated capillary of 50 μm i.d., 40 cm effective length, and an electric field of 160 V/cm. The length-of-read (LOR) achieved with this formulation to separate DNA sequencing extension products is greater and faster under similar conditions than the commercially supplied PAAm medium by Amersham Pharmacia, (725 bases vs. 625 bases) and faster (60 min. vs. 75 min.).

The method employed here to synthesize PAAm is straight-forward, simple and does not require cumbersome methods such as emulsion polymerization in order to achieve very high molecular weights. The resulting PAAm stock solution (4.5% w/v) can be uniformly diluted to the final concentration in ~24 hours. It also does not require the separation of PAAm from the reaction mixture prior to reconstituting PAAm to a final concentration. Furthermore, the formulation is prepared from a single average molecular weight PAAm and does not require a mixture of two different average molecular weights to achieve moderate viscosity and high-resolution.

The present invention provides consistency in synthesizing high molecular weight PAAm. This invention is a simple and consistent method of making very high viscosity average molecular weight (675 kDa to 725 kDa) PAAm; and separation medium formulated from this polymer yielded better resolution than the commercially supplied medium obtained from Amersham under identical separation conditions.

The materials and methods for experimental verification is described hereinafter four headings: Synthesis of PAAm Stock Solution, Dilution of PAAm Stock Solution to Final Concentration, Characterization of PAAm Separation Medium, and Capillary Electrophoresis and followed by a heading: Results and Discussion.

Synthesis of PAAm Stock Solution

Urea, ammonium persulfate (APS), and tetramethylethylenediamine (TEMED) were purchased from Aldrich Chemical Company (Milwaukee, Wis.). Acrylamide (40% w/v), tris[hyrdroxymethyl]aminomethane (TRIS), N-tris[hydroxymethyl]methyl-3-aminopropane-sulfonic acid (TAPS), and ethylenediaminetetra acetic acid (EDTA) were purchased from Sigma Chemical Company (St. Louis, Mo.).

To 144 mL of deionized water, added 105 g of urea and 28 mL of acrylamide (40% w/v) and bubbled the solution at room temperature for 1 hour with ultra-pure Argon (Air Liquide) at a flow-rate of ~0.5 L/min. Added to this, 62.5 μL of freshly made 10% (w/v) APS and 15.3 μL of TEMED under Argon atmosphere to initiate polymerization. Then the reaction mixture was immediately sealed and stored at 7° C. in a refrigerator. Polymerization was allowed to continue for ~24 hours at 7° C. to ensure maximum percent conversion of acrylamide to PAAm. This yields ~250 mL of 4.5% (w/v) PAAm stock solution with 7 M urea.

Dilution of PAAm Stock Solution to Final Concentration

A buffer concentrate of 10× TTE was made with 500 mM TRIS, 500 mM TAPS, and 20 mM EDTA. To 48.5 mL of deionized water, added 52.5 g of urea and 37.5 mL of 10× TTE buffer concentrate, which yielded 125 mL of TTE—urea buffer diluent.

This 125 mL of TTE—urea diluent was added to the above PAAm stock solution for dilution. The dilution was done at room temperature for ~24 hours by placing a magnetic stir bar in the mixture on a platform shaker (VWR) at 250 rpm.

This yields ~375 mL of a uniform solution of 3% (w/v) PAAm separation medium with 50 mM TRIS, 50 mM TAPS, 2 mM EDTA and 7 M urea.

Characterization of PAAm Separation Medium

The bulk viscosity of the separation medium was measured at 23° C. with a Brookfield viscometer (Brookfield Engineering Laboratories, Sloughton, Mass.) using spindle #4 at a speed of 1.5 rpm.

The viscosity average molecular weight ($M_v$) of freeze-dried PAAm was determined from intrinsic viscosity ($[\eta]$) value. The viscosity measurements were done in water at 25° C. using an Ubbelohde viscometer. The plot of reduced viscosity ($\eta_{red}$) versus polymer concentration when extrapolated to zero concentration gives ($[\eta]$) as intercept. The $M_v$ of PAAm was calculated from the $[\eta]$ value using Mark-Houwink equation ($[\eta]=kM^a$), for which $k=6.5\times10^{-3}$ (mL/g) and a =0.82 in water at 30° C. See Brandrup, J. et al (Eds.) Polymer Handbook, Wiley, New York, 1989.

Capillary Electrophoresis

Fused silica capillaries of 360 μm outside diameter from Polymicron Technologied (Tuscon, Ariz.) having an internal diameter of 50 μm were coated non-covalently with 1% (w/v) polydimethyl acrylamide (PDMA) solution to suppress electroosmotic flow (EOF) and DNA-capillary surface interactions (Madabhushi, Electrophoresis, 1998, 19,224–230). The PDMA was allowed to adsorb onto the capillary surface for a period of 1 hour after which time the unadsorbed PDMA was thoroughly washed off with deionized water.

BigDye DNA sequencing standard from Applied Biosystems (Foster City, Calif.) was dissolved in 40 μL of deionized water. An aliquot of 10 μL of the diluted DNA standard was denatured at 90° C. for 4 minutes and stored on ice before being used for electro-kinetic injection.

Electrophoresis was performed using an ABI Prism™ 310 Genetic Analyzer from Applied Biosystems. The total length of the capillary was 51 cm and the detection length was 40 cm. The coated capillary was filled with 3% (w/v) PAAm separation medium, and the cathode and anode chambers were filled with 1× TTE (50 mM TRIS, 50 mM TAPS, and 2 mM EDTA) buffer. A 1× TTE buffer (made from 10×concentrate from Amersham Pharmacia) was used in the cathode and anode chambers when evaluating the performance of PAAm medium from Amersham Pharmacia. The DNA standard was electro-kinetically injected for 4 seconds at a field of 60 V/cm, and the fragments were separated at 40° C. for 90 minutes at 160 V/cm.

The four-color raw data were multicomponent-analyzed with Genescan Analysis Software 672 from Applied Biosystems. Well separated single peaks from labeled T-reaction track were selected to evaluate the peak spacing per base (PSPB; mm) and the average full width at half-maximum (FWHM; mm). The plot of PSPB versus FWHM gives the approximate number of resolvable DNA fragments or the length-of-read (LOR) with a resolution value of 0.59 (Madabhushi, Electrophoresis, 1998, 19, 224–230).

Results and Discussion

The $M_v$ of PAAm was determined after dialyzing and freeze-drying the PAAm stock solution to remove impurities such as urea. The PAAm stock solution was dissolved in deionized water to give a solution of ~1% (w/v) for dialysis. Dialysis was done using a 12,000 molecular weight cut-off membrane from Sigma (St. Louis, Mo.) for ~72 hours by changing deionized water at regular intervals. Then the dialyzed PAAm solution was freeze-dried to get pure PAAm. The $[\eta]$ of PAAm was evaluated to be 3.91 dL/g and the $M_v$ was calculated to be ~674 kDa. The commercially supplied PAAm separation medium from Amersham Pharmacia was also similarly purified by dialysis and freeze-drying to yield PAAm. The $[\eta]$ of Amersham Pharmacia PAAm was evaluated to be 4.78 dL/g and the $M_v$ was calculated to be ~860 kD.

The viscosity of PAAm separation medium (3% w/v) measured at 23° C. using Brookfield viscometer with spindle #4 at a speed of 1.5 rpm was ~3300 cP. The viscosity of PAAm separation medium from Amersham Parmacia was found to be ~7400 cP under identical measuring conditions.

FIG. 1 shows the PSPB and FWHW against the base number for PAAm separation media by us as well as from Amersham Pharmacia. The capillary dimensions, coating and the electrophoretic conditions are essentially identical for all the cases. The LOR for 3% (w/v) PAAm medium was ~725 bases and was achieved in ~60 minutes. As a comparison, the LOR for Amersham Pharmacia PAAm was ~625 bases achieved in ~75 minutes. In order to evaluate the final concentration dependence of PAAm on separation performance, three different concentrations (2 w/v, 2.5% w/v, and 3% w/v) were studied. The LOR values for 2% and 2.5% (w/v) were found to be ~500 bases in ~45 minutes and ~575 bases in ~50 minutes, respectively. We routinely made at least 30 batches of PAAm separation medium using our recipe and for all the cases, the LOR values were found to be between ~700 to ~770 bases, and are higher than PAAm medium from Amersham Pharmacia.

The resolution value depends on the separation performance of the medium and is related to the PSPB. It also depends on the FWHM and is related to the electrophoretic conditions, EOF, DNA-surface interactions, etc. Durable and homogeneous coatings will reduce EOF as well as DNA-surface interactions more efficiently and decrease the FWHM. The resultant would be improved separation efficiency manifested in terms of increased LOR. In view of this, covalently coated PAAm capillaries from Biorad Laboratories (Hercules, Calif.), and covalently coated PDMA capillaries made in-house using Hjerten's method were studied under identical run conditions. See Hjerten, S., J. Chrom., 347, 191–198, 1985. The LOR values for a 3% (w/v) PAAm medium using covalent PAAm coating and covalent PDMA coating are ~625 bases and ~500 bases, respectively. Under similar coating conditions, the LOR values for Amersham Pharmacia PAAm medium are ~575 bases and ~500 bases, respectively. Although covalent PDMA coating is more durable than non-covalent coating, the latter seems to give longer LOR with a given separation medium. The loss of resolution may be due to coating inhomogeniety.

The following is a protocol for the synthesis of PAAm and the formulation of PAAm based separation medium made in accordance with the present invention, and the resolution analyses data of the thus formulated PAAm.

Upon dilution, the following recipe will yield 250 mL of 3% (w/v) polyacrylamide solution in 7M urea and 1× TTE (50 mM TRIS-50 mM TAPS-2 mM EDTA).

Special Notes to Read Before This Operation Procedure:
1) Acrylamide is a neurotoxin. Do not come in contact with acrylamide. Use of gloves, safety glasses and lab coat are a must.
2) Ammonium persulfate (APS) is a strong oxidizing agent. Do not leave it exposed to an oxygen environment for prolonged periods of time.
3) Store APS, tetramethyethylenediamine (TEMED) and acrylamide solutions in refrigerator with secondary container (plastic) to prevent any accidental spillage.

4) When TEMED arrives, some of TEMED solution should be transferred to a labeled small glass vial which has a polycone seal and date it. This is to decrease the risk of contamination of TEMED, which is highly toxic and a lachrymator, in the event of any spillage.

5) Always use secondary plastic containers when handling acrylamide, TEMED, and APS solutions to prevent any spillage.

Procedure:

I. Materials:
1. Urea (Aldrich, cat #U270-9)
2. Acrylamide (40% w/v) (Sigma, cat #A-4058)
3. Ammonium persulfate (APS) (Aldrich, cat #24,861-4)
4. Tetramethylethylenediamine (TEMED) (Aldrich, cat #41,101-9)
5. Tris[hydroxymethyl]aminomethane (TRIS) (Sigma, cat #T-1503)
6. N-tris[hydroxymethyl]methyl-3-aminopropane-sulfonic acid (TAPS) (Sigma, cat #T-9659)
7. Ethylenediaminetetraacetic acid (EDTA) (Sigma, cat #EDS)
8. Argon gas (ultra high purity) (Air Liquide)

II. Equipment:
1. Erlenmeyer flashes (2 L) (VWR)
2. Fume hood
3. Pipettes Pyrex (10 mL)
4. Platform shaker (VWR)
5. Stir plate
6. Parafilm (4 inch by 125 foot roll) (AMC)

III. Preparation of Stock Solutions:
1. 10× TTE (500 mM TRIS-500 mM TAPS-20 mM EDTA) buffer:
   a) Weigh out 3.03 g of TRIS in a 250 mL beaker.
   b) Add 50 mL of $dH_2O$.
   c) Add 0.29 g of EDTA, dissolve completely.
   d) Add 6.09 g of TAPS dissolve completely, cover and date.
2. 10% (w/v) APS solution for initiation of polymerization:
   a) Weigh out 0.1 g of APS.
   b) Transfer APS to a 2 mL cap tube.
   c) Add 1 mL of $dH_2O$ to tube with APS.
   d) Seal, label and date tube as 10% (w/v) APS.
   e) Shake on Vortex Genie2 for 30 sec. or until APS dissolves.
   f) Store APS in refrigerator (at around 7° C.) until ready to use.
3. TTE-urea solution for dilution of polyacrylamide:
   a) Weigh out 52.5 g of urea.
   b) Add 48.5 mL of $dH_2O$ to urea and dissolve.
   c) Then add 37.5 mL of a 50 mL 10× TTE solution (500 mM TRIS-500 mM TAPS-20 mM EDTA)
   d) The total solution volume will be around 125 mL.
   e) Refrigerate the solution (at around 7° C.) until needed.

IV. Polymerization of 4.5% (w/v) Acrylamide:
1) In a 2 L Erlenmeyer flask add 105.0 g of urea.
2) Add 144 mL of $dH_2O$ and dissolve urea.
3) Add 28 mL of 40% (w/v) acrylamide solution.

Note: Acrylamide is neurotoxic, so use all the protective equipment and read the MSDS for handling and waste disposal of acrylamide.

4) Bubble gently with Argon gas for 1 hour using 10 mL Pyrex pipette submerged in solution.

Note: Do not bubble vigorously as the solution will froth and may spill.

5) Remove APS stock solution from refrigerator.
6) Remove TEMED from refrigerator.
7) Cut 2 pieces of parafilm (must be large enough to seal flask and contents from outside air).
8) Under Argon atmosphere add 62.5 $\mu$L (micro liter) of APS.
9) Re-submerge 10 mL pipette in solution for approximately 10 sec.
10) Remove pipette far enough to allow aliquoting of TEMED.
11) Under presence of Argon add 15.3 $\mu$L (micro liter) of TEMED (do not submerge pipette in solution as the TEMED may evaporate).
12) Immediately seal flask by not exposing the solution to outside air.
13) Store the flask in refrigerator (at around 7° C.) for 24 hrs.
14) Come back in one hour to verify solution has changed its viscosity significantly.

Note: If after 1 hour, there is no significant change in solution viscosity, it indicates the failure of polymerization step. Pour the contents of the flask carefully into the appropriate hazardous waste container and start a fresh batch for polymerization.

V. Dilution of 4.5% (w/v) polyacrylamide to the Final Concentration of 3% (w/v):
1) Add 125 mL of TTE-urea stock solution to the 4.5% (w/v) polyacrylamide solution at room temperature.
2) Once polyacrylamide solution and TTE-urea come in contact, break polymer free from bottom of the flask. This can be done by using a 10 mL plastic pipette.
3) Place 2 inch by ⅜ inch stir bar in flask with the polymer solution.
4) Cover with parafilm enough to keep out debris.
5) Place and secure flask with polymer solution on platform shaker.
6) Turn on platform shaker and set at 150 rpm.
7) After 24 hours of mixing at room temperature, the polymer will be a homogenous mixture.
8) Remove polymer from flask, place in 2 mL tubes and store them around 7° C.

In summary, we have developed a procedure to routinely make PAAm separation medium for high resolution separation of DNA sequencing products. This procedure is simple, straight-forward, does not require isolation of PAAm before being reconstituted, and hence may prove to be cost-effective in production sequencing environment. If care is taken not to expose the reaction mixture to air while initiation and polymerization, then this procedure yields high molecular weight PAAm, which is quintessential in obtaining increased LOR values. The routine synthesis and uniform dissolution of PAAm stock solution to a final concentration can be finished in ~48 hours. The viscosity of the final solution is still on the high level, but more manageable.

It has thus been shown that the present invention provides high molecular weight polyacrylamides having a viscosity average molecular weight of about 675–725 kDa, which were synthesized by conventional red-ox polymerization. The method of this invention is straightforward, simple, and does not require cumbersome methods such as emulsion polymerization in order to achieve very high molecular weights. Further, the PAAm formulation of this invention does not require separation of PAAm from the reaction mixture prior to reconstituting the polymer in a final concentration. In addition, the formulation of this invention is prepared from a single average mol. wt. PAAm as opposed to the mixture of two different average mol. wt. PAAm required to achieve high resolution by prior known formulation techniques.

While specific formulation procedures, parameters, materials, etc. have been set forth to exemplify and teach the principles of the invention, such are not intended to be limiting. Modifications and changes may become apparent to those skilled in the art, and it is intended that the invention be limited only by the scope of the appended claims.

What is claimed is:

1. A polyacrylamide medium having a viscosity average molecular weight of about 675–725 kDa.

2. The polyacrylamide medium of claim 1, prepared from a single average molecular weight polyacrylamide.

3. The polyacrylamide medium of claim 2, produced by optimizing concentrations of acrylamide monomer, ammonium persulfate, and tetramethylethlene-diamine in an aqueous medium and polymerizing at sub-ambient temperatures after removing oxygen from the reaction mixture by bubbling ultra-pure argon, and further diluting to a final concentration with an electrophoretic buffer.

4. The polyacrylamide medium of claim 2, wherein synthesize of the polyacrylamide medium is carried out without emulsion polymerization, and without separation of the polyacrylamite from the reaction mixture prior to reconstituting the polyacrylamide in a final concentration.

5. The polyacrylamide medium of claim 1, when utilized as a separation medium in a capillary electrophoreis of DNA, produces a single base resolution of ~725 bases in ~60 minutes in a non-covalently coated capillary.

6. A formulation for polyacrylamides having a viscosity average molecular weight of about 675–725 kDa, including:

synthesizing the polyacrylamides by conventional red-ox polymerization.

7. The formulation of claim 6, wherein the synthesizing is carried out by:

mixing concentration of acrylamide monomer, ammonium persulfate, and tetramethylethylenediamine in an aqueous medium, polymerizing at sub-ambient temperatures after removing oxygen from the reaction mixture, and diluting the resultant polymer solution to a final concentration with an electrophoretic buffer.

8. The formulation of claim 7, wherein removing oxygen from the reaction mixture is carried out by bubbling ultra-pure argon.

9. The formulation of claim 7, wherein the electrophoretic buffer is selected from the group consisting of TRIS-TAPS-EDTA, and Trisborate.

10. The formulation of claim 7, wherein the aqueous medium is selected from the group consisting of water, urea and buffer.

11. The formulation of claim 7, wherein the sub-ambient temperature is in the range of 0° to 15° C.

12. The formulation of claim 7, wherein the final concentration of the polymer solution is in a range from 2% to 4%.

13. The formulation of claim 7, additionally including utilizing the formulation as a separation medium for capillary electrophoresis of DNA sequencing standard.

14. The formulation of claim 13, wherein a single base resolution of ~725 bases in achieved in ~60 minutes.

15. The formulation of claim 14, wherein the capillary electrophoresis is carried out in a non-covalently coated capillary.

16. In a polyacrylamide medium for the electrophoretic separation of biomolecules, the improvement comprising:

a polyacrylamide having a viscosity average molecular weight of about 675–725 kDa.

17. The improvement of claim 16, wherein said polyacrylamide has a composition of at least acrylamide monomer, ammonium persulfate, and tetramethy-lethylenediamine.

18. The improvement of claim 16, wherein said polyacrylamide is synthesized by red-ox polymerization technique.

19. The improvement of claim 17, wherein the composition of said polyacrylamide is synthesized in an aqueous medium and polymerized at sub-ambient temperatures following moving oxygen from the reaction mixture.

20. The improvement of claim 19, additionally including diluting the thus formed solution to a final concentration with an electrophoretic buffer.

21. The improvement of claim 20, wherein the oxygen is removed by bubbling ultra-pure argon, and wherein the electrophoretic buffer is composed of TRIS-TAPS-EDTA.

22. The improvement of claim 16, wherein the polyacrylamide is composed of a single average molecular weight polyacrylamide.

23. The improvement of claim 18, wherein the polyacrylamide is synthesized without emulsion polymerization.

24. The improvement of claim 18, wherein the polyacrylamide is synthesized without separation of the polyacrylamide from the reaction mixture prior to reconstituting the polyacrylamide to a final concentration.

25. The improvement of claim 18, wherein synthesis and uniform dissolution of a PAAm stock solution to a final concentration is carried out in about 48 hours.

* * * * *